United States Patent [19]

Reuter et al.

[11] Patent Number: 5,105,004
[45] Date of Patent: Apr. 14, 1992

[54] AROMATIC ETHERS

[75] Inventors: Knud Reuter; Dieter Freitag, both of Krefeld; Günther Weymans, Leverkusen; Rolf Dhein, Krefeld; Paul J. Mayska, Krefeld; Karsten-Josef Idel, Krefeld; Volker Eckhardt, Krefeld; Uwe Westeppe, Mettmann, all of Fed. Rep. of Germany

[73] Assignee: Bayer Aktiengesellschaft, Leverkusen, Fed. Rep. of Germany

[21] Appl. No.: 612,653

[22] Filed: Nov. 13, 1990

Related U.S. Application Data

[63] Continuation of Ser. No. 416,909, Oct. 4, 1989, abandoned.

[30] Foreign Application Priority Data

Oct. 12, 1988 [DE] Fed. Rep. of Germany ....... 3834661
Jun. 28, 1989 [DE] Fed. Rep. of Germany ....... 3921165

[51] Int. Cl.$^5$ .......................................... C07C 255/00
[52] U.S. Cl. .................... 558/389; 558/416; 558/419; 560/56; 560/59; 562/468
[58] Field of Search ....................... 558/389, 416, 419; 560/56, 59; 562/468

[56] References Cited

U.S. PATENT DOCUMENTS 3,716,583  2/1973  Nakamura et al. .................... 560/62
3,873,593  3/1975  Heath et al. ......................... 260/465
3,944,583  3/1975  Quinn ............................... 260/343.4

OTHER PUBLICATIONS

Surrey, *Name Reactions in Organic Chemistry*, 244–245, Academic Press, 1961.
"Makromolekulare Stoffe"—pp. 1418–1429, 1456, 1522, 1524, 1527–1534.

*Primary Examiner*—Marianne Cintins
*Assistant Examiner*—Jessica H. Nguyen
*Attorney, Agent, or Firm*—Joseph C. Gil; Richard E. L. Henderson

[57] ABSTRACT

The new aromatic ethers of the formulae

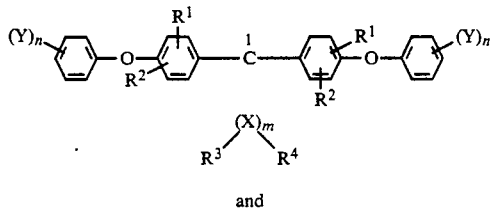

and

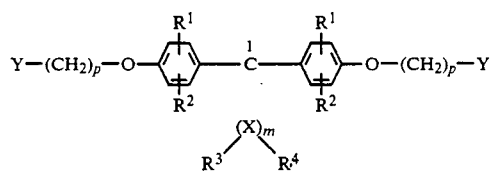

can be used for the preparation of plastics which, in turn, can be processed further to give moulded articles, films, foils and filaments. The plastics prepared from the new aromatic ethers are distinguished by exceptional dimensional stability under heat.

2 Claims, No Drawings

AROMATIC ETHERS

This application is a continuation of application Ser. No. 07/416,909 filed Oct. 4, 1989 now abandoned.

The invention relates to new aromatic ethers, a process for their preparation and the use of the new aromatic ethers for the preparation of plastics and plastic mixtures which can be processed further to give moulded articles, films, foils and filaments.

The invention relates to new aromatic ethers of the formulae

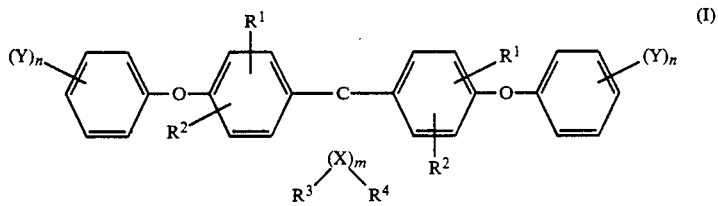

(I)

and

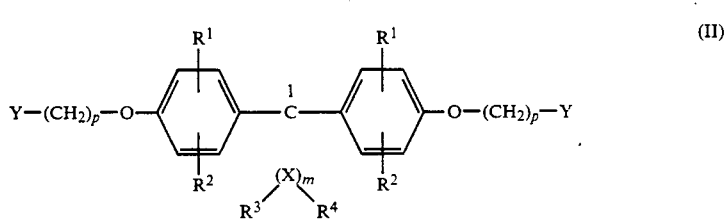

(II)

in which $R^1$ and $R^2$ independently of one another denote hydrogen, halogen, $C_1$-$C_8$—alkyl, $C_5$-$C_6$—cycloalkyl, $C_6$-$C_{10}$—aryl or $C_7$-$C_{12}$—aralkyl, $R^3$ and $R^4$ can be chosen individually for each X and independently of one another denote hydrogen or $C_1$-$C_{12}$—alkyl, X represents carbon with the proviso that at least one ring carbon atom is simultaneously substituted by two $C_1$-$C_{12}$—alkyl radicals, Y represents CN or $COOR^5$ with $R^5$ being H, $C_1$-$C_6$—alkyl, $C_5$-$C_6$—cycloalkyl or $C_6$-$C_{10}$—aryl, n denotes 1 or 2, m is an integer from 4 to 7 and p represents an integer from 1 to 4.

Possible halogens of the above-mentioned formula are, for example, fluorine, chlorine and bromine, in particular bromine and chlorine, possible alkyl radicals are the methyl, ethyl, n- and iso-propyl and n-, iso-and tert.-butyl radical, preferably the methyl radical, possible cycloalkyl radicals are the cyclopentyl and cyclohexyl radical, preferably the cyclohexyl radical, possible aryl radicals are the phenyl and naphthyl radical, preferably the phenyl radical, and possible aralkyl radicals are the benzyl and cumyl radical, preferably the cumyl radical. In the above-mentioned formula, n preferably represents the number 1, m the numbers 4 and 5, in particular the number 5, and p the numbers 1, 2 and 3, and in particular the numbers 1 and 2.

Preferably 1 to 2 ring carbon atoms (X), in particular only 1 ring carbon atom (X) of the formulae (I) and (II), is/are simultaneously substituted by $R^3$ and $R^4$, the substitution of the carbon atoms in the β-position to C-1 being preferred.

Preferred aromatic ethers are those of the formulae

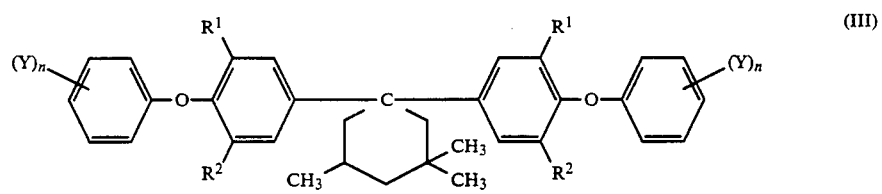

(III)

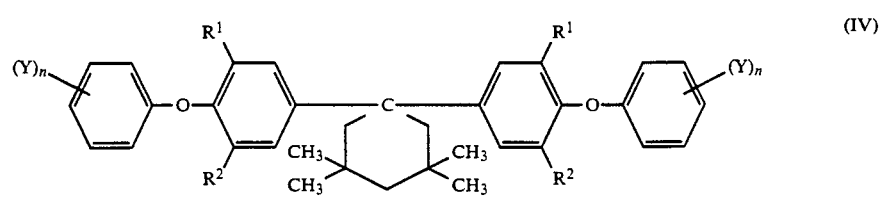

(IV)

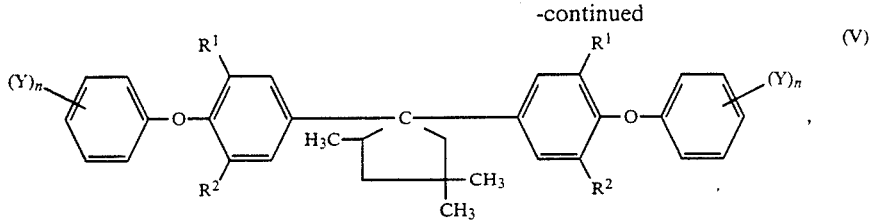

in which

R¹, R², Y and n have the meaning mentioned for formula (I).

Particularly preferred aromatic ethers of the formula (II) are those in which the radicals R¹ and R² independently of one another denote hydrogen or methyl and n represents the number 1. Especially preferred compounds of the formula (II) are those in which R¹ and R² denote hydrogen and n represents the number 1.

The present invention further relates to a process for the preparation of aromatic ethers of the formulae (I) and (II)

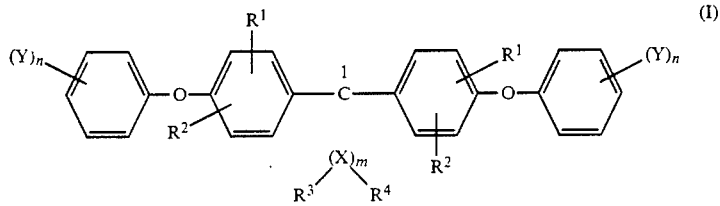

and

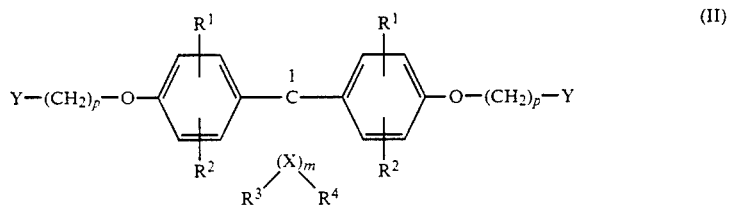

in which

R¹ and R² independently of one another denote hydrogen, halogen, $C_1$–$C_8$-alkyl, $C_5$–$C_6$-cycloalkyl, $C_6$–$C_{10}$-aryl or $C_7$–$C_{12}$-aralkyl, R³ and R⁴ can be chosen individually for each X and independently of one another denote hydrogen or $C_1$–$C_{12}$-alkyl, X represents carbon with the proviso that at least one ring carbon atom is simultaneously substituted by two $C_1$–$C_{12}$-alkyl radicals, Y represents CN or COOR⁵ with R⁵ being $C_1$–$C_6$-alkyl, $C_5$–$C_6$-cycloalkyl or $C_6$–$C_{10}$-aryl, n denotes 1 or 2, m is an integer from 4 to 7 and p represents an integer from 1 to 4, which is characterized in that compounds of the formula (VI)

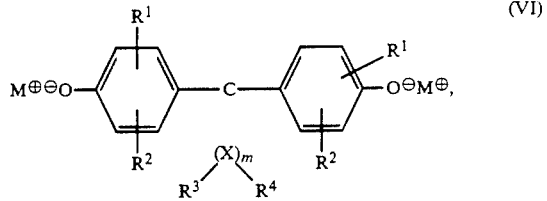

in which

R¹, R², R³, R⁴, X and m have the above-mentioned meaning and

M represents an alkali metal, in particular lithium, sodium or potassium, are reacted with compounds of the formula

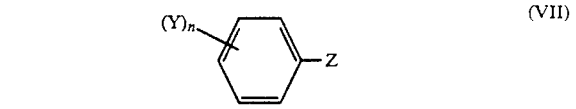

or $$Y-(CH_2)_p-Z, \qquad (VIII)$$

in which

Y, n and p have the above-mentioned meaning and

Z represents fluorine, chlorine, bromine or the nitro group, preferably fluorine, chlorine or the nitro group, at temperatures from 20° to 350° C., preferably 50° to 250° C., in particular 80° to 100° C., in the presence of a dipolar aprotic solvent.

Dipolar aprotic solvents which may be preferably mentioned are: acetonitrile, diethylene glycol dimethyl ether, N,N-dimethylacetamide, N-methylpyrrolidone, N-methylcaprolactam, diphenylsulphone, N,N-dimethyl-formamide, N,N'-dimethylimidazolidin-2-one (DMI) and/or dimethyl sulphoxide, most preferably dimethyl sulphoxide and DMI. It is also possible to replace a part, preferably up to about 50% by weight, of the dipolar aprotic solvents by non-polar solvents, such as toluene, xylene, mesitylene, chlorobenzene, cyclohexane and/or petroleum ether.

The amount of solvent employed can vary within a wide range. In general, about 0.5 to 50, preferably 2 to 20, parts by weight of solvent, relative to the total amount of compounds of the formula (V) and (VI), are employed. Reference is made in this connection to U.S. Pat. No. 3,873,593, in which more detailed explanations of the process described above can be found.

The compounds of the formula (VI) are employed in amounts of about 2 to 3 moles, preferably 2 to 2.5 moles, relative to 1 mole of the compound of the formula (VII).

The compounds of the formula (VII) employed are known and described, for example, in U.S. Pat. Nos. 3,873,593, 3,763,210 and 3,787,475.

The aromatic dihydroxy compounds from which the salts of compound (VI) are derived can be prepared by condensation of the appropriate phenols in a manner known per se with the appropriate ketones in the presence of acidic catalysts and, if desired, further cocatalysts. Reference is made in this connection to German Patent Application P 38 32 3966 and to Schnell, Chemistry and Physics of Polycarbonates, Interscience Publishers, New York, 1964.

Examples of possible compounds of the formula (VI) to be employed in the process according to the invention are:

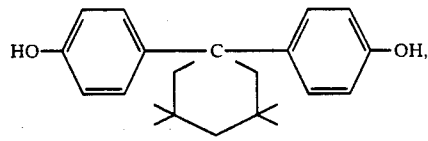

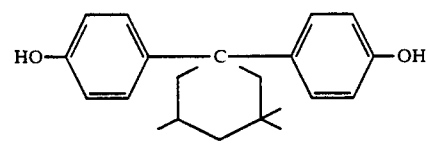

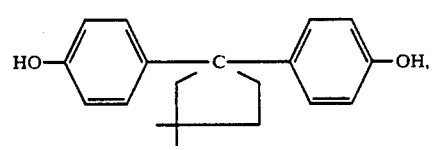

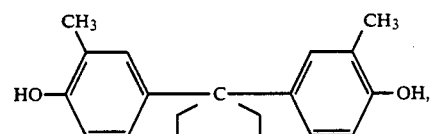

and particularly preferably

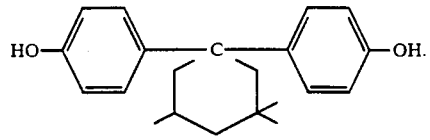

Examples of compounds of the formula (VII) which can be employed are

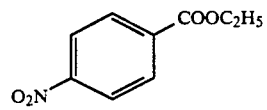

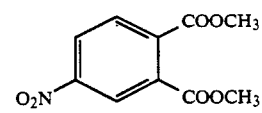

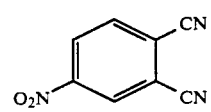

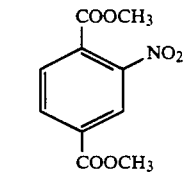

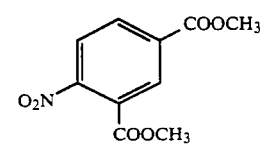

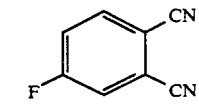

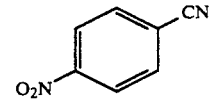

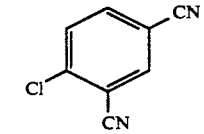

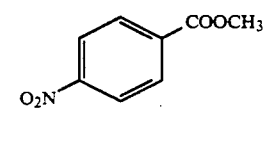

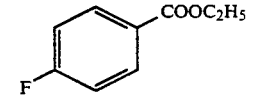

-continued

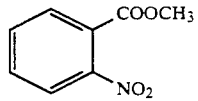,

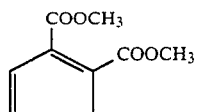,

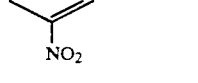,

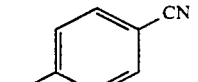,

Br—CH₂COOC₂H₅,

Br—CH₂—CN, Cl—CH₂COOH,

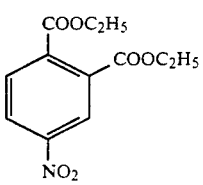, preferably

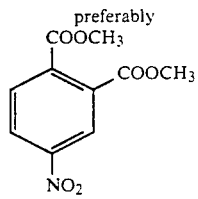,

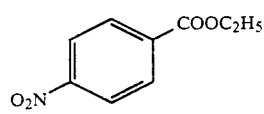

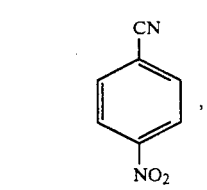,

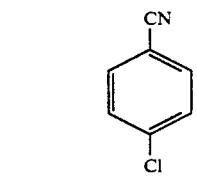,

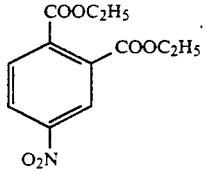

-continued

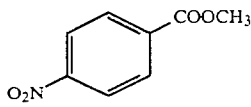, particularly preferably

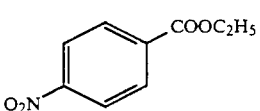,

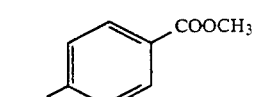,

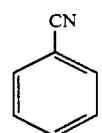,

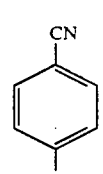,

The present invention further relates to the use of the new aromatic ethers for the preparation of polymers, in particular thermoset materials and thermoplastics. The polymers prepared from the new aromatic ethers can, in turn, be used for the preparation of moulded articles, films, filaments and foils.

For example, the new aromatic ethers can be employed for the preparation of polyether imides, aromatic polyesters, aliphatic/aromatic polyesters, polyamides (aromatic and aliphatic/aromatic), thermoset materials by cyclotrimerization of the nitrile groups, polyether ketones, preferably for the preparation of polyether imides, polyesters and polyamides, most preferably for the preparation of aromatic and aromatic/aliphatic polyesters and aromatic and aromatic/aliphatic polyamides.

In order to prepare the polymers from the new aromatic ethers, the aromatic ethers are polycondensed in a customary manner with the other possible comonomers for the individual polymers. The preparation of the above-mentioned polymers can in this case be carried out by the methods known from the literature, for example via the carboxylic anhydrides, carboxylic esters the free carboxylic acids or amides (by hydrolysis of the esters or nitriles) or the acid chlorides (see, for example, Houben-Weyl, supplementary and subsequent volumes to the 4th edition (1987), volume E20 "Makromolekulare Stoffe" (Macro-molecular Substances) Part 2, pages 1418-1429, 1456, 1522, 1524, 1527-1534 or directly from the compounds of the formulae (I) and (II).

Of course, it is also possible to blend the polymers prepared from the new aromatic ethers in a customary manner and in customary mixing proportions with one another or with other known polymers, such as polycarbonates, polyester carbonates, polyesters, polyimides, polyamides, polyether imides, polyether ketones, polyether sulphones and/or aromatic polyethers.

The polymers prepared from the new aromatic ethers have particularly good dimensional stability under heat compared to comparable polymers based on known dihydroxydiphenylcycloalkanes.

EXAMPLES

EXAMPLE 1

15.5 g of the bisphenol

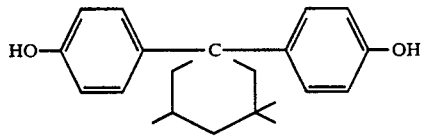

(0.05M), 8.9 g of 45% strength sodium hydroxide solution (0.1M), 100 ml of dimethyl sulphoxide and 60 ml of toluene are refluxed under $N_2$ in a stirring apparatus having a water separator until no more water is separated. The water separator is then replaced by a Soxhlet apparatus which is charged with molecular sieve 4 Å. The mixture is relfuxed unter $N_2$ for 1 h and the Soxhlet apparatus is then replaced by a descending condenser. The mixture is distilled (mainly toluene) until an internal temperature of 145° C. is reached. 23.4 g of ethyl p-nitrobenzoate are then added and the reaction mixture is reacted unter $N_2$ at 120° C. for 12 h. The mixture was cooled, poured into a large amount of $H_2O$ and extracted by shaking repeatedly with methylene chloride. The methylene chloride phases were evaporated by distillation. The residue (11 g) was identified by NMR spectroscopy as mainly

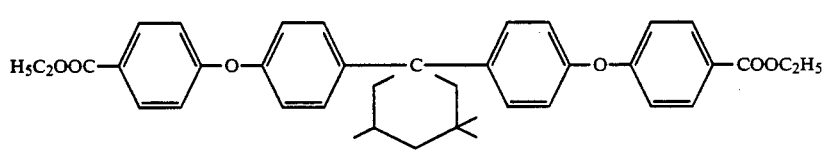

EXAMPLE 2

46.41 g (0.15 mol) of bis-(4-hydroxyphenyl)-3,3,5-trimethylcyclohexane, 42.08 g (0.30 mol) of 40% potassium hydroxide solution, 80 g of N,N'-dimethylimidazolidin-2-one (DMI) and 100 ml of toluene are introduced into a 500 ml three-necked flask equipped with a stirrer, thermometer, water separator and reflux condenser and the mixture is then refluxed until all the water has been removed from the system. Then 41.25 g (0.30 mol) of p-chlorobenzonitrile are added and the reaction mixture is heated to 195° C. After a reaction time of 6 hours the reaction mixture is concentrated in a rotary evaporator and the residue is recrystallized from n-butanol.

The yield of the isolated product was 67%. The product displayed the following properties:
Melting point: 175° C.
Total chlorine content: 0.009%
Inorganic chlorine: 16 ppm

| Elemental analysis: | C | H | N | O |
|---|---|---|---|---|
| theoretical | 82.0 | 6.29 | 5.46 | 6.24 |
| found | 82.2 | 6.60 | 5.67 | 6.40 |

The $^1H$ and $^{13}C$ NMR spectra correspond to the chemical formula:

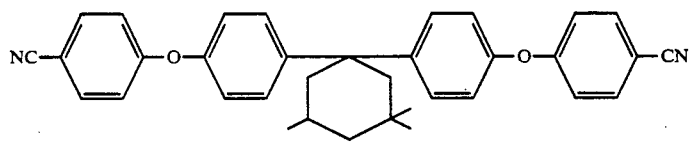

Example 3

20.46 g (0.04 mol) of 1,1-bis[4-(cyanophenoxy)-phenyl]-3,3,5-trimethylcyclohexane (from Example 2), 44.8 g (0.4 mol) of 50% potassium hydroxide solution and 50 ml of DMI are weighed into a 250 ml three-necked flask equipped with a stirrer, thermometer, gas inlet tube and reflux condenser. The reaction mixture is refluxed for 24 h, accompanied by the introduction of nitrogen. During the reaction ammonia is split off and the nitrile which was initially only slightly soluble gradually dissolves. In the end the solution is clear. The progress of the reaction is monitored by examining the evolution of ammonia and by measuring the acid number of precipitated product samples. When the reaction has ended the product is isolated by precipitation in 600 ml of dilute hydrochloric acid and subsequent filtration.

The yield was quantitative. The product displayed the following properties:

melting point: 273° C. (acetic acid)
acid number (AN): 203–205 (theoretical: 204)

| Elemental analysis: | C | H | O |
|---|---|---|---|
| theoretical | 76.34 | 6.22 | 17.43 |
| found | 76.20 | 6.33 | 17.60 |

The $^1H$ and $^{13}C$ NMR spectra confirm the following chemical formula:

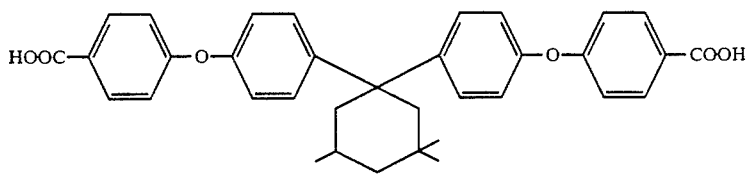

Example 4

23,29 g of the bisphenol:

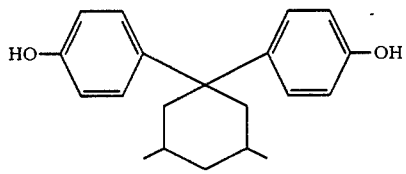

(0.075M), 13.35 g of 45% sodium hydroxide solution (0.15M), 100 ml of dimethyl sulphoxide and 65 ml of toluene are refluxed under $N_2$ in a stirring apparatus equipped with a water separator until no more water is separated. Then the water separator is replaced by a Soxhlet apparatus which is charged with molecular sieve 4 Å.

The mixture is refluxed for 1 hour under $N_2$ and the Soxhlet apparatus is then replaced by a descending condenser. The mixture is distilled (mainly toluene) until an internal temperature of 145° C. is reached. Then 24.44 g of 4-nitrobenzonitrile (0.165M) are added and the reaction mixture is reacted at 100° C. for 7 hours under $N_2$. The mixture was cooled and the crystals which separated out were filtered off, washed with $H_2O$ and then with methanol and dried.

Yield: 24.92 g (65% of theory)
Melting point: 177°–178° C.

| Elemental analysis: | C | H | N |
|---|---|---|---|
| theoretical: | 82.0 | 6.29 | 5.46 |
| found: | 81.7 | 6.55 | 5.66 |

The $^1H$ spectrum and the IR spectrum correspond to the following chemical formula:

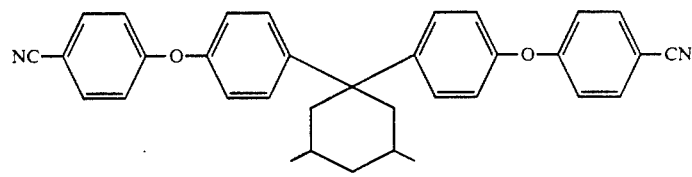

Example 5

Following the same procedure as Example 1 but with a reaction time of 13 h at 150° C., 23.3 g of the bisphenol:

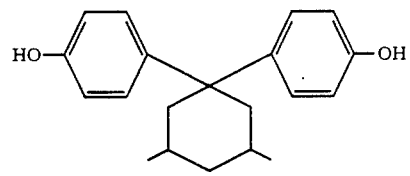

(0.075M), 13.35 g of 45% sodium hydroxide solution (0.15M), 100 ml of dimethyl sulphoxide and 65 ml of toluene and 39.5 g of nitroterephthalic acid (0.165M) are reacted. After cooling the reaction mixture it was filtered, $H_2O$ was added and extraction was then carried out with methylene chloride. The $CH_2Cl_2$ phase was evaporated by distillation and the residue was re-precipitated from toluene/petroleium ether (yield: 19 g) and identified as essentially

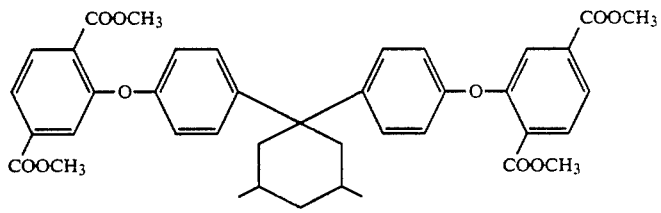

Example 6

60,8 g of the dicarboxylic acid:

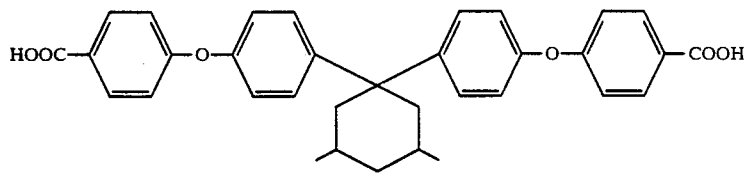

(prepared according to Example 3 or by hydrolysis of the ester from Example 1) were refluxed for 15 hours in 130 g of thionyl chloride. Then the excess thionyl chloride was distilled off, the residue was dissolved in $CH_2Cl_2$ and the solution was filtered and the $CH_2Cl_2$ was distilled off again. 46.7 g of the acid chloride:

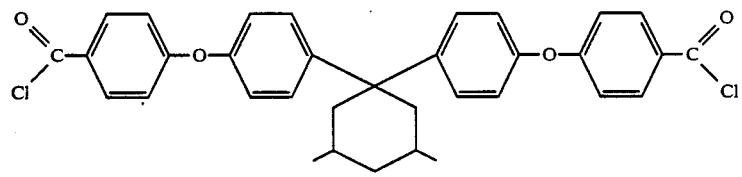

were isolated as the residue.

Example 7

A solution of 14.69 g (0.025M) of the acid chloride

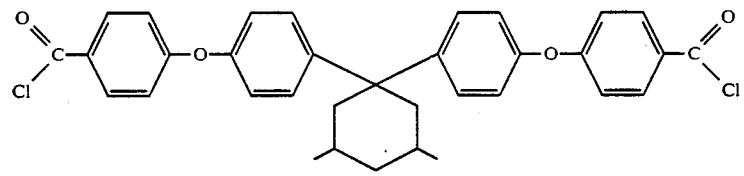

(from Example 6), 7.65 g of terephthaloyl chloride (0.0375M) and 7.65 g of isophthaloyl chloride (0.0375M) in 100 ml of $CH_2Cl_2$ was added dropwise with thorough stirring at 23° C. over a period of 15 mins. to a mixture of 10 g of NaOH (0.25M), 560 ml of $H_2O$, 22.8 g of bisphenol A (0.1M), 0.966 g of tetra-n-butylammonium bromide and 450 ml of $CH_2Cl$. Then the mixture was stirred for a further hour at 23° C. The $CH_2Cl_2$ phase was then washed with $H_2O$. 33.8 g of an amorphous, aromatic polyester of high dimensional stability under heat ($T_g$=189° C.) were then isolated from the $CH_2Cl_2$ phase by evaporating off the solvent, from which polyester tear-resistant films are for example obtained. The relative viscosity of the polyester was $\eta_{rel}$=1.336 (5 g/l; $CH_2Cl_2$; 25° C.).

We claim:

1. An aromatic ether of the formula

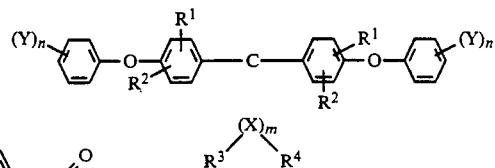

in which
R$^1$ and R$^2$ independently denote hydrogen, halogen, $C_1$-$C_8$-alkyl, $C_5$-$C_6$-cycloalkyl, phenyl, naphthyl, benzyl, or cumyl,
R$^3$ and R$^4$ are chosen independently for each X and independently denote hydrogen or $C_1$-$C_{12}$-alkyl,
X represents carbon, with the proviso that at least one carbon atom is simultaneously substituted by two $C_1$-$C_{12}$-alkyl radicals,
Y represents CN or COOR$^5$, with R$^5$ being H, $C_1$-$C_6$-alkyl, $C_5$-$C_6$-cycloalkyl, phenyl, or naphthyl,
n is 1 or 2,
m is an integer from 4 to 7, and
p is an integer from 1 to 4.

2. A method for the production of plastics and plastic mixtures comprising polycondensing an aromatic ether of claim 1.

* * * * *

UNITED STATES PATENT AND TRADEMARK OFFICE
CERTIFICATE OF CORRECTION

PATENT NO. : 5,105,004

DATED : April 14, 1992

INVENTOR(S) : Knud Reuter et al

It is certified that error appears in the above-identified patent and that said Letters Patent is hereby corrected as shown below:

ON THE TITLE PAGE:

In the Abstract on the face of the patent, delete the formulae and insert the following therefor:

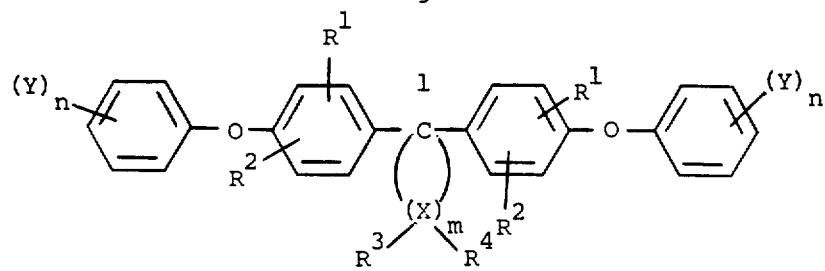

and

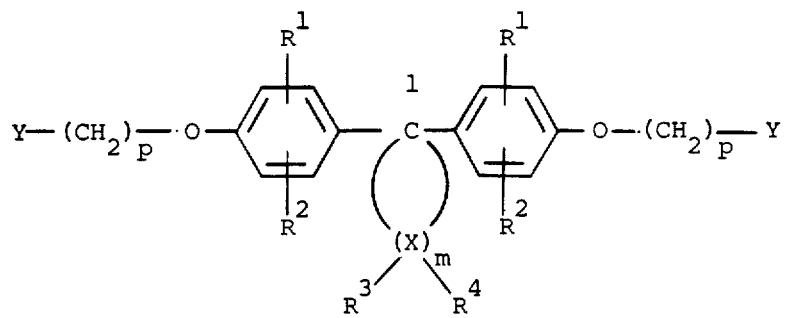

UNITED STATES PATENT AND TRADEMARK OFFICE
CERTIFICATE OF CORRECTION

PATENT NO. : 5,105,004

DATED : April 14, 1992

INVENTOR(S) : Knud Reuter et al

It is certified that error appears in the above-identified patent and that said Letters Patent is hereby corrected as shown below:

At column 1, please delete formulae (I) and (II) and insert the following therefor:

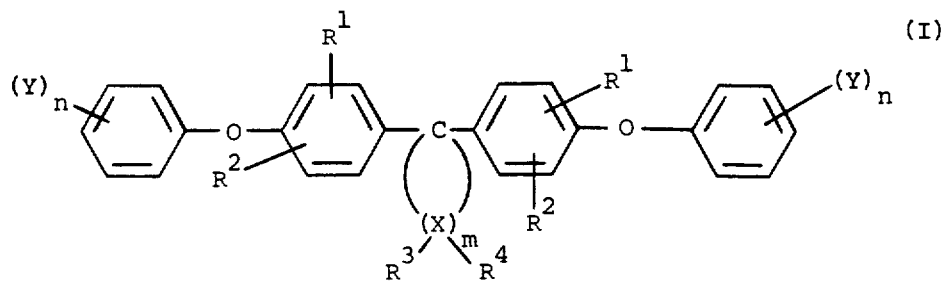

(I)

and

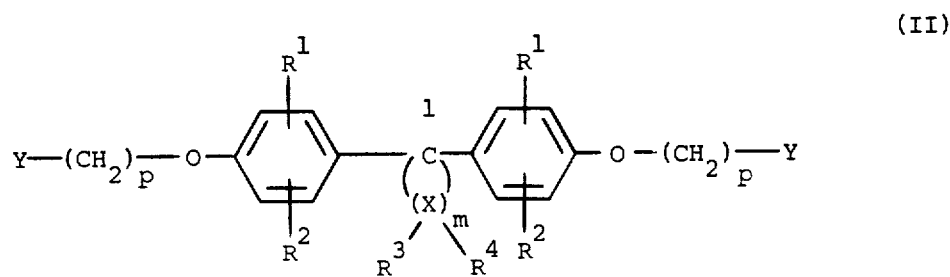

(II)

UNITED STATES PATENT AND TRADEMARK OFFICE
CERTIFICATE OF CORRECTION

PATENT NO. : 5,105,004

DATED : April 14, 1992

INVENTOR(S) : Knud Reuter et al

It is certified that error appears in the above-identified patent and that said Letters Patent is hereby corrected as shown below:

In the specification at column 3, please delete formulae (I) and (II) and insert the following therefor:

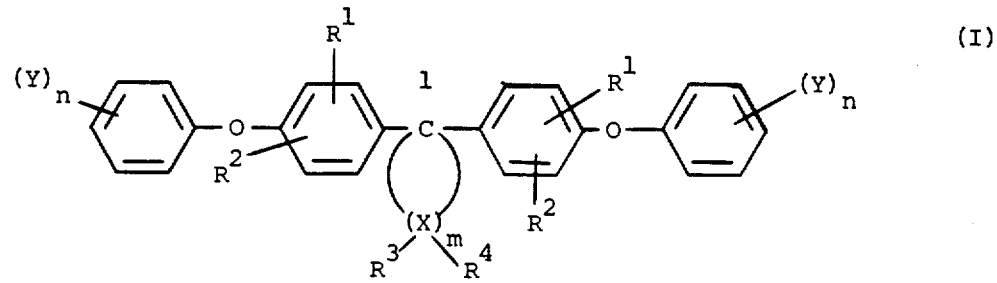

(I)

and

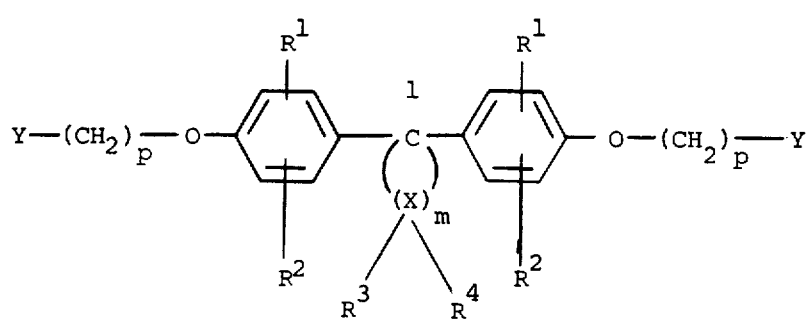

(II)

UNITED STATES PATENT AND TRADEMARK OFFICE
CERTIFICATE OF CORRECTION

PATENT NO. : 5,105,004

DATED : April 14, 1992

INVENTOR(S) : Knud Reuter et al

It is certified that error appears in the above-identified patent and that said Letters Patent is hereby corrected as shown below:

In the specification at column 4, please delete formula (VI) and insert the following therefor:

(VI)

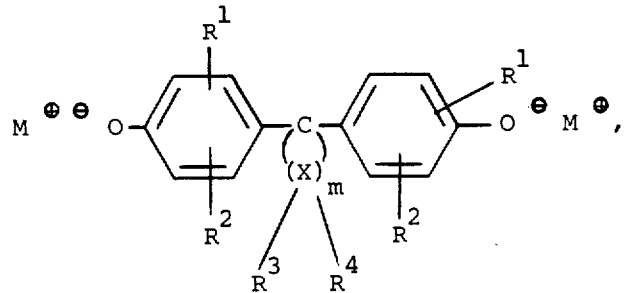

UNITED STATES PATENT AND TRADEMARK OFFICE
CERTIFICATE OF CORRECTION

PATENT NO.  : 5,105,004
DATED       : April 14, 1992
INVENTOR(S) : Knud Reuter et al It is certified that error appears in the above-indentified patent and that said Letters Patent is hereby corrected as shown below:

In Claim 1 at column 14, please delete the formula and insert the following therefor:

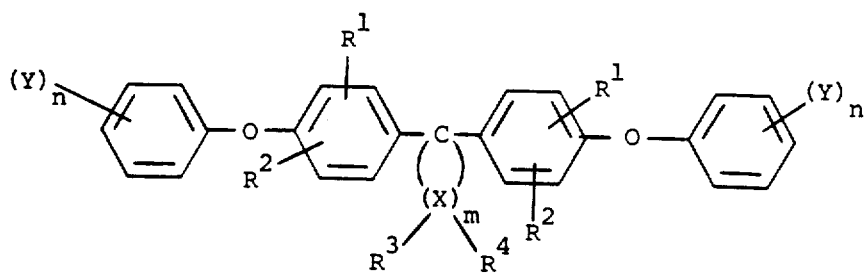

Signed and Sealed this

Twenty-first Day of September, 1993

Attest:

*Attesting Officer*

BRUCE LEHMAN

Commissioner of Patents and Trademarks